United States Patent
Cavazza

(10) Patent No.: US 6,329,358 B1
(45) Date of Patent: Dec. 11, 2001

(54) PHARMACEUTICAL COMPOSITION SUITABLE FOR STIMULATING THE MULTIPLICATION AND GROWTH OF OSTEOBLASTS

(75) Inventor: Claudio Cavazza, Rome (IT)

(73) Assignee: Sigma-Tau Industrie Farmaceutiche Riunite S.p.A, Rome (IT)

( * ) Notice: Subject to any disclaimer, the term of this patent is extended or adjusted under 35 U.S.C. 154(b) by 0 days.

(21) Appl. No.: 09/402,653

(22) PCT Filed: Apr. 3, 1998

(86) PCT No.: PCT/IT98/00076
§ 371 Date: Oct. 8, 1999
§ 102(e) Date: Oct. 8, 1999

(87) PCT Pub. No.: WO98/46233
PCT Pub. Date: Oct. 22, 1998

(30) Foreign Application Priority Data

Apr. 16, 1997 (IT) .............................................. RM97A0217

(51) Int. Cl.$^7$ .......................... A61K 31/56; A61K 31/205
(52) U.S. Cl. ............................ 514/171; 514/127; 514/556
(58) Field of Search .................................. 514/171, 167, 514/177, 556; 424/440

(56) References Cited

U.S. PATENT DOCUMENTS 5,326,569 * 7/1994 Acosta et al. ........................ 424/440
5,945,412 * 8/1999 Fuh et al. .............................. 514/176

* cited by examiner

Primary Examiner—Theodore J. Criares
(74) Attorney, Agent, or Firm—Nixon & Vanderhye

(57) ABSTRACT

A pharmaceutical composition consisting essentially of an alkanoul L-camitine wherein the alkanoyl group is linear or branched and as 2–8 carbon atoms, dehydroepiandrosterone or.dehydroepiandrosterone sulphate.

12 Claims, No Drawings

PHARMACEUTICAL COMPOSITION SUITABLE FOR STIMULATING THE MULTIPLICATION AND GROWTH OF OSTEOBLASTS

This application is a 35 U.S.C. §371 of PCT/IT98/00076 filed Apr. 3, 1998.

The present invention relates to a drug which, by stimulating the multiplication and growth of osteoblasts, is useful in the treatment of bone tissue pathologies both of a traumatic nature, such as fractures, and those related to ageing, such as osteoporosis.

Bone fractures are a widespread pathology in all age brackets. Young people and adults in the vast majority of cases suffer bone fractures as a result of traumatic events caused mainly by sporting activities or by road accidents, whereas elderly people are subject to such pathology as a result of the greater fragility of the bone caused by osteoporosis.

The hospitalisation period for patients with bone fractures, which may last from a few days to several months, depends to a large extent on the type of fracture, the age of the patient and his or her general condition.

The period of convalescence varies in length and depends on the severity of the pathology. At the end of this period the patient returns to hospital for roentgeno-graphic investigations and for the determination of bone callus formation.

Unfortunately, not all patients present the same degree of healing and some of them present poor and sometimes incomplete formation of the bony callus. On account of these events, the patient is obliged to remain inactive for a further period of time, with loss of work days and additional hospital expenses.

To date there are no specific therapeutic measures which act directly on the bone cells, or osteoblasts, specifically favouring their multiplication with formation of bone callus and healing of the injury. In departments of orthopaedic surgery, adjuvant therapy for fractures is given in the form of calcitonin or bisphosponates (e.g. alendronate), specific drugs for the prevention of post-menopausal osteoporosis, possibly in combination with vitamins, particularly vitamin D, and mineral salts.

On this basis, the discovery of new drugs acting directly on the osteoblasts and favouring their multiplication and the formation of bone callus, and thus capable of reducing average healing time, would have a beneficial effect on the patient by bringing about a reduced recovery time. In view of the substantial numbers of such patients, the socio-economic benefit is clear in terms of the resulting savings in health-care expenditure and the increase in days worked during the year.

The object of the present invention is therefore to provide a drug which overcomes the limitations and unsatisfactory efficacy of the therapeutic agents currently used and accelerates bone callus formation and the healing of fractures by stimulating the growth and proliferation of osteoblasts.

This object is achieved according to the present invention through the co-ordinated use of lower alkanoyl L-carnitines or their pharmacologically acceptable salts together with dehydroepiandrosterone (DHEA) or dehydro-epiandrosterone sulphate (DHEA-S), where what is meant by "coordinated use" of the afore-mentioned compounds is either the co-administration, i.e. the substantially simultaneous administration, of said active ingredients, or the administration of a combination composition containing a mixture of said active ingredients, in addition to any appropriate excipients or other active ingredients.

The present invention, moreover, also relates to pharmaceutical compositions containing the above-mentioned active ingredients which can be administered by the oral, parenteral, rectal or transdermal routes and are suitable for promoting the formation of bone callus and the healing of fractures.

Previous uses of the alkanoyl derivatives of L-carnitine are well known.

For example, acetyl-L-carnitine has been used for the treatment of pathological disturbances of the CNS, particularly Alzheimer's disease and diabetic neuropathy; propionyl-L-carnitine has been used for treating peripheral vascular diseases and congestive heart failure.

Other therapeutic uses of alkanoyl derivatives of L-carnitine are known and have been extensively reported in the literature.

Although dehydroepiandrosterone and dehydroepiandrosterone sulphate are hormones which have been known for many years now, it is only recently that researchers have been increasingly focusing their attention on these substances.

The metabolic role and activity of these hormones have yet to be fully clarified.

Recent clinical data show a relationship between a decrease in DHEA (S) and age-related diseases such as cardiac ischaemia (Barrett-Connor E, Edelstein SL. A prospective study of dehydroepiandrosterone sulfate and cognitive function in an older population. F Am Geriat Soc 1994; 42: 420–23); variations in the amounts or distribution of body fats (Williams DP, Boyden T W, Pamenter R W, Lohman T G, Coing S B. Relationship of body fat percentage and fat distribution with dehydroepiandrosterone sulfate in premenstrual females. F Clin Endocrinol Metab 1993; 77: 80–85); onset of non-insulin-dependent diabetes mellitus and some forms of cancer (Ebeling P, Kiovisto A. Physiological importance of dehydroepi-androsterone. Lancet 1994; 343: 1479–91).

KM Chiu, N Binkley, A Shug and S. Grayenstein in J Bone Miner Res, 9 (Suppl 1), S354, 1994, describe the activity of alkaline phosphatase (ALP) on "osteoblast-like cells" taken from the bone marrow of pig and monkey femurs and have found that this activity is modulated and promoted by the presence of L-carnitine and DHEA-S. In the same study, the investigators report that DHEA-S is capable of inducing the synthesis and increasing the activity of carnitine acyl transferase enzymes, thus promoting the transport of fatty acids across the mitochondrial membrane.

Both these mechanisms of action give rise to a substantial increase in βoxidation only if they are well synchronised, since L-carnitine is the limiting element in the production of energy induced by DHEA (Battelli D, Bellei M, Kneer N, Baccaranti Contri M, Pasquali Ronchetti I, Bobyleva V, Lardy H A. Effects of dehydro-epiandrosterone and carnitine treatment on rat liver. Biochem Mol Biol Int 1994, Vol/Iss/Pg 33/6: 1063–71).

These complementary mechanisms of action and the enhancement of osteoblast-specific alkaline phosphatase activity mean that, in the presence of an adequate, co-ordinated supply of these two compounds, the osteoblasts are suitably stimulated to replicate and are able to draw upon a greater amount of energy essential for sustaining repair processes, i.e. formation of bone callus and healing of fractures.

Surprisingly, it has now been found that the lower alkanoyl L-carnitines which will be specified here below in combination with DHEA or DHEA-S synergically promote the formation and proliferation of osteoblasts to a distinctly greater extent than L-carnitine in combination with the same hormones.

The alkanoyl L-carnitines useful for the new therapeutic use of the present invention are those in which the linear or branched alkanoyl has 2–8 carbon atoms, and preferably 2–6 carbon atoms.

Acetyl, propionyl, butyryl, valeryl and isovaleryl L-carnitine are particularly preferred.

What is meant by a pharmacologically acceptable salt of alkanoyl L-carnitine is any salt of the latter with an acid that does not give rise to unwanted toxic or side effects.

These acids are well known to pharmacologists and to experts in pharmacy.

Non-limiting examples of such salts are chloride, bromide, orotate, acid aspartate, acid citrate, acid phosphate, fumarate and acid fumarate, lactate, maleate and acid maleate, acid oxalate, acid sulphate, glucose phosphate, tartrate and acid tartrate.

In the compositions of the present invention the weight-to-weight ratio of DHEA or DHEA-S to the alkanoyl L-carnitine is in the 0.001:1 to 0.1:1 range.

The compositions of the present invention may also additionally comprise vitamins, mineral salts, antioxidants and vegetable fibres and may present themselves in solid, powder, granular or liposomal form in tablets, capsules, granules, powders, or ampoules for oral, parenteral, rectal or topical use.

By way of non-limiting examples a number of compositions according to the invention are given here below. For the sake of brevity and simplicity, reference will be made only to acetyl L-carnitine, it being understood that the compositions described may apply to all the above-mentioned alkanoyl L-carnitines and their pharmacologically acceptable salts.

Examples of Compositions

1. Acetyl L-carnitine 500 mg, DHEA-S 50 mg, α-tocopherol acetate 1 mg, vitamin $D_2$ 15 μg.
2. Acetyl L-carnitine 1000 mg, DHEA-S 50 mg, α-tocopherol acetate 1 mg, vitamin $D_2$ 15 μg.
3. Acetyl L-carnitine 500 mg, DHEA-S 50 mg, α-tocopherol acetate 1 mg, β-carotene 2 mg, vitamin $D_2$ 15 μg, selenium 0.05 mg, zinc 2.5 mg, magnesium 10 mg.
4. Acetyl L-carnitine 500 mg, DHEA-S 50 mg, α-tocopherol acetate 1 mg, β-carotene 2 mg, vitamin $D_2$ 15 μg, selenium 0.05 mg, zinc 2.5 mg, magnesium 10 mg, cobalt 0.5 mg.
5. Acetyl L-carnitine 1000 mg, DHEA-S 50 mg, α-tocopherol acetate 1 mg, β-carotene 2 mg, vitamin $D_2$ 15 μg, selenium 0.05 mg, zinc 2.5 mg, manganese 1 mg, magnesium 10 mg, cobalt 0.5 mg.

What is claimed is:

1. An orally, parenterally, rectally or transdermally administrable pharmaceutical composition, for promoting formation of bone callus and healing of fractures, which composition together with a pharmacologically acceptable excipient consists essentially of, as its active ingredients, an alkanoyl L-carnitine, wherein the alkanoyl group is linear or branched and has 2 to 8 carbon atoms or a pharmacologically acceptable salt thereof, and dehydroepiandrosterone or dehyrdoepiandrosterone sulphate.

2. The pharmaceutical composition of claim 1, wherein the alkanoyl group has 2 to 6 carbon atoms.

3. The pharmaceutical composition of claim 1, wherein the alkanoyl L-carnitine is selected from the group consisting of acetyl, propionyl, butyryl, valeryl and isovaleryl L-carnitine.

4. The pharmaceutical composition of claim 1, wherein the active ingredients are acetyl L-carnitine and dehydroepiandrosterone sulphate.

5. The composition of claim 1, 2, 3 or 4, wherein the weight-to-weight ratio of dehydroepiandrosterone or dehydroepiandrosterone sulphate to the alkanoyl L-carnitine is in a range of 0.001:1 to 0.1:1.

6. The composition of claim 1, 2, 3, 4 or 5 further comprising a vitamin, mineral salt, antioxidant or vegetable fiber.

7. The composition of claim 1 presented in solid, semisolid, liquid, semiliquid, powder, granular or liposomal form in tablets, capsules, granules, powders, or ampoules for oral, parenteral, rectal or topical use.

8. A method of promoting formation of bone callus and healing of bone fractures consisting essentially of the coordinated administration to a patient of an effective amount of an alkanoyl L-carnitine, wherein the alkanoyl has 2 to 8 carbon atoms or a pharmacologically acceptable salt thereof, and hydroepiandrosterone or hydroepiandrosterone sulphate.

9. The method of claim 8, wherein the alkanoyl group has 2 to 6 carbon atoms.

10. The method of claim 8, wherein the alkanoyl L-carnitine is selected from the group consisting of acetyl, propionyl, butyryl, valeryl and isovaleryl L-carnitine.

11. The method of claim 8, wherein the active ingredients are acetyl L-carnitine and dehydroepiandrosterone sulphate.

12. The method of claim 11, wherein the weight-to-weight ratio of dehydroepiandrosterone sulphate to acetyl L-carnitine administered is in a range of 0.001:1 to 0.1:1.

* * * * *